CAMELLIA
Filed Sept. 26, 1975
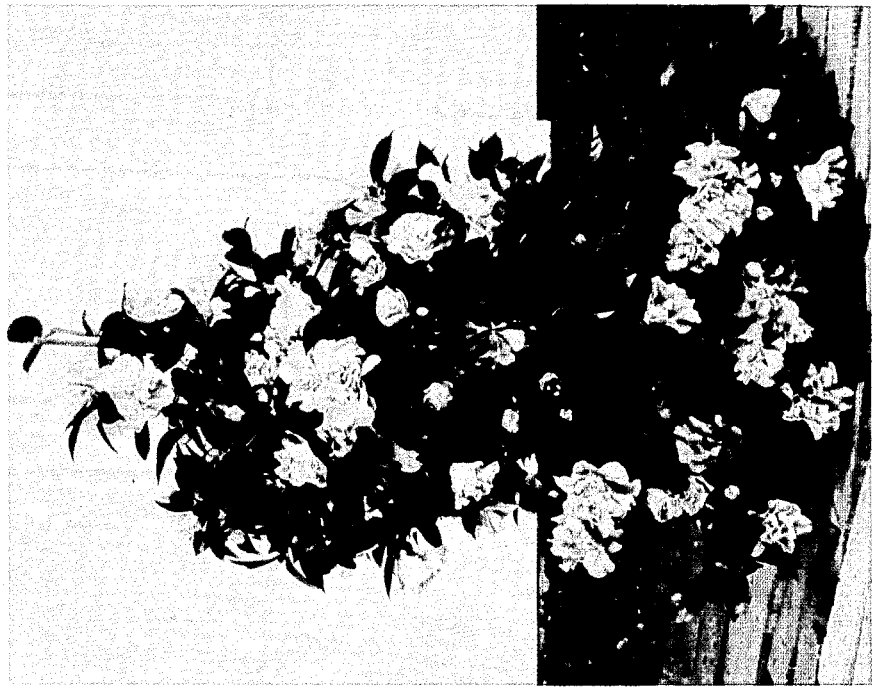
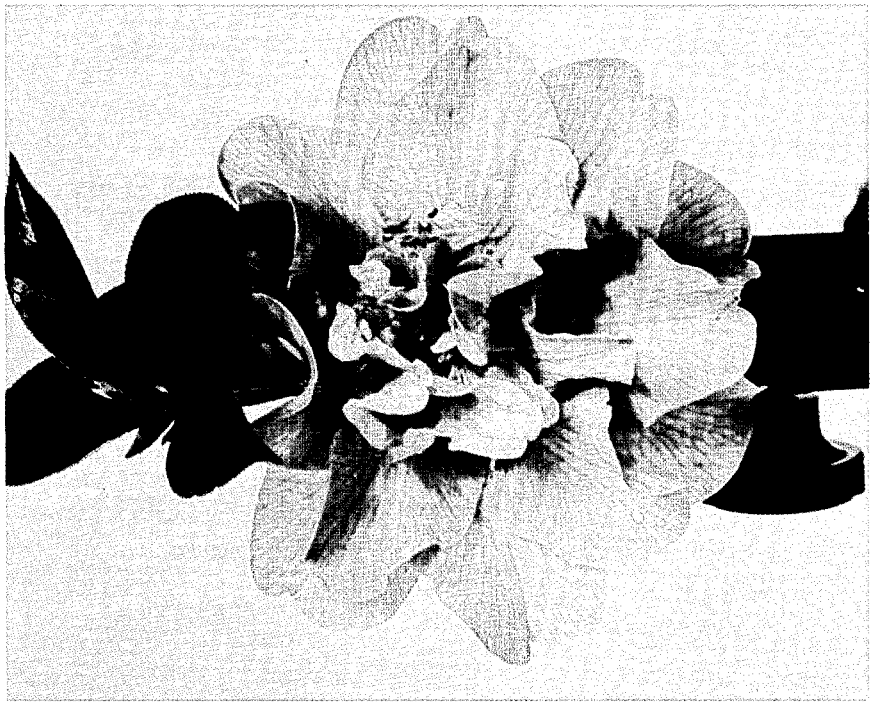

United States Patent

Plant Pat. 3,966
Patented Oct. 26, 1976

3,966
CAMELLIA

Earl D. Hudson, Hemet, Calif., assignor to Monrovia Nursery Company, Azusa, Calif.

Filed Sept. 26, 1975, Ser. No. 617,058
Int. Cl.[2] A01H *5/00*
U.S. Cl. Plt.—61 1 Claim

ABSTRACT OF THE DISCLOSURE

A new and distinct variety of Camellia, originating as a seedling of *Camellia japonica,* "Pink Parfait," as the seed parent and an unknown pollen parent. The new Camellia cannot be reproduced from seed, but it has been extensively propagated by cutting, and to a lesser extent by grafting, and by selection of the asexually reproduced plants, a stabilized new plant has been developed. The new plant is characterized by novel features not found in the seed parent, and distinctive from any known Camellia plant. The most outstanding features of novelty of the new Camellia plant are: a habit of extremely dense upright growth; the production of profuse displays of pink flower clusters, which include closely packed bouquets of flowers at the tips of the branches; and an unusual combination of flower color (Pink Rose Bengal 25/2) and leaves having a glossy dark green upper surface and light green under surface.

The Camellia which is the subject of this application first germinated in March 1965, in my nursery garden in Sun Valley, Calif. The original plant was asexually produced by the Monrovia Nursery Company, in Azusa, Calif. The first flowers were observed in December 1971. The seed parent of the original plant was *Camellia japonica* Pink Parfait, and, although the pollen parent is unknown, it is probable that it was a *Camellia japonica* pollen parent.

All present plants have been reproduced asexually (mostly by cuttings, but also by grafting) from the original plant of March 1965. The plant has never been offered for sale to the public. The plant has never been described in any publication. As will be seen from the following description of the plant, it takes over the coloring of the known seed parent, but is very distinct from the seed parent, and can be readily identified from any known previously existing variety of Camellia. In the description of the plant which follows, and in the foregoing abstract, the British Horticultural Colour Charts are used by reference, for the identification of plant color.

The plant, as described, may be seen in the accompanying drawings, which are color photographs showing both the distinctive coloring of the plant and its distinctive characteristic growth.

DESCRIPTION OF THE PLANT

*Parentage*

Seed Parent: *Camellia japonica* Pink Parfait
Pollen Parent: Another *Camellia japonica* of unknown variety

*Growth habit*

The plant exhibits an extremely dense upright growth habit with very sturdy branches. The branches tend to be short, and slow in growth. The bark coloring on the young branches is reddish-brown, while on the older branches it is gray. Features that distinguish this new variety from its seed parent are the clusters of medium-size pink, incomplete double flowers and its characteristics of being a mid-to-late season bloomer.

*Foliage*

The leaves are of good texture, 2¾"–3½" long, and 1"–1⅞" wide, with a petiole of about ⅜" long. Their coloring is glossy dark green above and light green beneath, with prominent mid-ribs and veins.

*Flowers*

The plant is a mid-to-late season bloomer. The flowers are incomplete double, with petaloids, 3½"–4½" wide and 2½" deep. Their color is Rose Bengal 25/2. The inflorescences are attractive, appearing mostly in clusters, as in a bouquet, at the tips of the branches, and occasionally as single displays throughout the plant. The stamens are a pale yellow. The flowers remain intact until they drop from the pant after blooming. The blooming period will last over a period of two to three months.

I claim:

A new and distinct variety of Camellia, as described.

No references cited.

ROBERT E. BAGWILL, Primary Examiner